United States Patent
Baruffi et al.

(10) Patent No.: US 9,637,533 B2
(45) Date of Patent: May 2, 2017

(54) METHODS FOR INCREASING THE EMBRYO IMPLANTATION RATE IN MAMMALS

(75) Inventors: Marcelo Dias Baruffi, Ribeirao Preto (BR); Erika da Silva Carvalho Morani, Jaboticabal (BR); Marcelo Roncoletta, Jaboticabal (BR); Camillo del Cistia Andrade, Ribeirao Preto (BR); Lilian Cataldi Rodrigues, Ribeirao Preto (BR)

(73) Assignees: UNIVERSIDADE DE SÃO PAULO-USP, São Paulo-SP (BR); INPRENHA BIOTECHNOLOGIA E DESENVOLVIMENTO AVANçADO LTDA-ME, Jaboticabal-SP (BR)

( * ) Notice: Subject to any disclaimer, the term of this patent is extended or adjusted under 35 U.S.C. 154(b) by 51 days.

(21) Appl. No.: 13/996,920

(22) PCT Filed: Dec. 9, 2011

(86) PCT No.: PCT/BR2011/000454
§ 371 (c)(1),
(2), (4) Date: Sep. 16, 2013

(87) PCT Pub. No.: WO2012/083396
PCT Pub. Date: Jun. 28, 2012

(65) Prior Publication Data
US 2014/0057858 A1    Feb. 27, 2014

(30) Foreign Application Priority Data
Dec. 21, 2010 (BR) ................................. 1005702

(51) Int. Cl.
*A61K 38/17* (2006.01)
*C07K 14/47* (2006.01)
*C07K 14/705* (2006.01)

(52) U.S. Cl.
CPC ........ *C07K 14/7056* (2013.01); *A61K 38/178* (2013.01); *A61K 38/1732* (2013.01); *C07K 14/4726* (2013.01)

(58) Field of Classification Search
CPC .............. A61K 38/1732; A61K 38/178; C07K 14/1732; C07K 14/7056; C07K 14/4726
See application file for complete search history.

(56) References Cited

U.S. PATENT DOCUMENTS

2003/0091972 A1* 5/2003 Gardner et al. ................... 435/2
2007/0185014 A1   8/2007 Dartt

FOREIGN PATENT DOCUMENTS

EP    1908476 A1    9/2008
WO    2012083396 A1    6/2012

OTHER PUBLICATIONS

Blois, S.M, et al. A pivotal role for galectin-1 in fetomaternal tolerance. Nature Medicine, 2007, vol. 13, No. 12, p. 1450-1457.*
Mazurek, N., et al. Phosphorylation of the beta-galactoside-binding protein galectin-3 modulates binding to its ligands. Journal of Biological Chemistry, 2000, vol. 275, No. 46, p. 36311-36315.*
Young S. Choe, et al; Expression of Galectin-1 mRNA in the Mouse Uterus is Under the Control of Ovarian Steroids During Blastocyst Implantation; Molecular Reproduction and Development 48:261-266 (1997); Korea; (XP009155938).
Shaye K. Lewis, et al; Galectin 15 (LGALS15): A Gene Uniquely Expressed in the Uteri of Sheep and Goats that Functions in Trophoblast Attachment; Biology of Reproduction 77, 1027-1036(2007); USA; (XP009155943).
Farmer, J., et al., "Galectin 15 (LGALS15) functions in trophectoderm migration and attachment", The FASEB Journal, Feb. 2008, pp. 548-560, vol. 22.

* cited by examiner

*Primary Examiner* — Robert Landsman
*Assistant Examiner* — Bruce D Hissong
(74) *Attorney, Agent, or Firm* — Alston & Bird LLP

(57) ABSTRACT

The present invention relates to a method for increasing embryo implantation rate in mother's uterus in mammals by administering to the uterus of a mammal an effective amount of beta-galactoside-binding lectin or derivatives thereof, as well as to a product comprising said lectin.

15 Claims, No Drawings

METHODS FOR INCREASING THE EMBRYO IMPLANTATION RATE IN MAMMALS

CROSS-REFERENCE TO RELATED APPLICATIONS

This application is the U.S. National Stage of International Application No. PCT/BR2011/000454, filed Dec. 9, 2011, which designates the U.S. and was published by the International Bureau in English on Jun. 28, 2012, and which claims the benefit of Brazilian Patent Application No. PI 1005702-1, filed Dec. 21, 2010, all of which are hereby incorporated by reference in their entirety.

FIELD OF THE INVENTION

The present invention relates to a method for increasing embryo implantation rate in mother's uterus in mammals by administering to the uterus of a mammal an effective amount of beta-galactoside-binding lectin or derivatives thereof, as well as to a product comprising said lectin.

DESCRIPTION OF THE RELATED ART

Agricultural industry plays a key role in Brazilian economy, thanks to its considerable share in Gross National Product and positive contribution to the balance of trade.

To ensure its profitability at the agricultural market, an agricultural property should maintain maximal reproductive effectiveness of livestock in order to meet the consumers demand for high-quality products. In this sense, the maintenance of adequate birth rates is a key factor at the chain of events which results in a profitable agricultural property. Nevertheless, in most cases, maintaining optimal reproduction levels is a difficult task due to high rates of early pregnancy embryo loss.

Reproduction can be defined as the conception of living beings from the same species after a sequence of physiological events, which, in turn, rely on a multiplicity of factors. The use of state-of-the-art reproduction techniques at the agricultural area can have a key role in genetic improvement of livestock, increasing pregnancy potential (implantation of embryos into the mother's uterus) in order to ensure maximum productivity during the working life of an animal.

However, throughout the world, embryo loss is one of the most common causes for economic loss to breeders; therefore, the prevention of early embryo loss is still a challenge in view of the complex mechanisms involved in the diagnosis and maintenance of pregnancy.

Early diagnose, which identifies embryo implantation rate into mother's uterus in mammals is a key tool for agricultural procedures, since it allows breeders to adopt preventive measures and minimize eventual economic loss. Hence, new technologies are developed in view of the improved knowledge of the reproductive physiology of the ovary of cattle to achieve better reproductive results and reduce treatment costs.

Similarly to in vitro fertilization of cattle, assisted reproductive techniques are becoming increasingly popular, due to market needs. The effective reproductive performance of cattle is directly related with the birth of a great number of female calves from breeds of dairy cattle and male calves from breeds of beef cattle, thus earning economic profits for agricultural properties.

Other market features, such as the global consumer demand for quality, scale and standardization of products of animal origin, together with the struggle for space for breeding, agricultural and bioenergy areas stimulate the search for higher productivity, causing reproduction biotechniques to improve at a fast pace.

In line with production and consumption needs of the global primary market, Brazilian agricultural industry relies on assisted reproductive techniques to increase the average productivity of cattle herds, since said techniques substantially increase the birth of genetically superior animals.

The main reproduction techniques used in agricultural properties include: (i) mating or reproduction by natural means; (ii) artificial insemination; (iii) in vivo production followed by embryo transfer; and (iv) in vitro production followed by embryo transfer. Regardless of the chosen technique, the main object of the reproduction method is to allow maximum performance of the reproducing species, achieving positive results.

Mating is a widely used technique since it is less expensive for breeders, but it has limited control of sexually transmissible diseases and provides slower genetic improvement of herds. In this procedure, embryos consist of 50% genetic material from the father (therefore, different from the genetic material from the mother), which may cause the formation of a high number of alloantigens and lead to embryo loss due to lack of maternal-fetal tolerance.

An alloantigen is any molecule encoded by the genetic material from other organism belonging to the same species. Since said molecule is a different one and it is introduced into another organism, the immune system of the latter is induced to produce a series of responses against the "extraneous" material. An example is the newly fertilized embryo, which is half genetic material from the mother and half genetic material from the father; the latter half may be extraneous to the mother's immune system, and thus it may be rejected by the mother's organism. The absence of maternal-fetal immune tolerance (process by which the mother's organism recognizes/accepts the fetus without triggering an immune response against it) is one of the main causes of precocious abortion.

Another reproduction technique widely used in the agricultural area is artificial insemination (AI), which consists in artificially depositing semen (spermatozoon/male gamete and seminal plasma) in the female reproductive tract by means of specific techniques suitable for the anatomic particularities of each female. AI success is measured by the pregnancy rate—or the number of pregnant females in view of the number of inseminated females. In this procedure, the generated embryos also consist of 50% genetic material from the father (therefore, different from the genetic material from the mother), which therefore may also lead to the formation of a high number of alloantigens and lead to embryo loss due to the absence of maternal-fetal tolerance.

Additionally, in vivo production followed by embryo transfer (ET) is a reproduction technique wherein several embryos are generated in the reproductive tract of a donor female (who donates the genetic material) and transferred to the uterus of a receptor female from the same species, which will carry pregnancy to term. The generation of embryos into the uterus of donors involves superovulation, artificial insemination and embryo flushing techniques. After flushing, embryos are evaluated and the viable ones may be transferred or cryopreserved. The transfer (deposition) of embryos from in vivo production into the uterus or uterine horn of receptors depends on processes for the synchronization of estrus (i.e., to adapt the receptor's uterus to the same stage of embryonic development). In this procedure, embryos transferred to the receptor's organism consist of up to 100% alloantigens (different genetic material), since they are entirely composed of genetic material from the donors and from the father, which implies in a higher risk of embryo loss due to the absence of maternal-fetal tolerance.

On the other hand, in vitro fertilization followed by embryo transfer relates to the generation of embryos in laboratory, and said embryos are transferred to the uterus of receptor females from the same species, which would carry the pregnancy into term. Laboratory production of embryos depends on the following: (i) aspiration of oocytes from the donor's ovarium by means of ultrasound guided follicular puncture; (ii) IVM—in vitro maturation of oocytes followed by in vitro induction of oocyte cytoplasm and oocyte nucleus maturation, thus preparing the egg for fertilization; (iii) IVF—in vitro fertilization or process of syngamy of mature oocytes and capable spermatozoons; (iv) IVC—in vitro cultivation of embryos after fertilization until said embryos reach the proper stage (morula and/or blastocyst) for transfer after 5-7 days cultivation; (v) embryo transfer, when—after the cultivation period—the embryos should be evaluated and those with good viability may be transferred, cryopreserved and/or vitrified. The transfer of in vitro produced embryos in the uterus or uterine horn of receptors also depends on processes for the synchronization of estrus (i.e., to adapt the receptor's uterus to the same stage of embryonic development). In this procedure, embryos ovulated in the receptor's organism consist of up to 100% alloantigens (different genetic material), since they are entirely composed of genetic material from the donors and from the father, which implies in higher risks of embryo loss due to absence of maternal-fetal tolerance.

As described above, maternal-fetal tolerance is an immune process which regulates the response of the mother's organism against the embryo or fetus. The immune system of an organism is responsible for a complex set of reactions to external factors and/or aggressors which may impair its regular physiological state.

Immunoregulatory responses during pregnancy are events incurring from ovulation, copula and fertilization which, above all, aim at the growth and development of the conceptus (embryo or fetus and associated membranes).

In this sense, Lewis, S. K. et al, 2007 (*Galectin-15 [LGALS15]: A Gene Uniquely Expressed in the Uteri of Sheep and Goats that Functions in Trophoblast Attachment*) observed that, in ruminants, the embryo at MO stage (morula, between days 4-6) enters the uterus and continues its development up to the BL stage (blastocyst, between days 6-7), which contains a monolayer of cells called trophectoderm cells. After the rupture of the zona pellucida up to day D12 ($12^{th}$ day) in sheep, or D15 ($15^{th}$ day) in goats, embryos remain at the elongation phase. During said phase the trophectoderm produces interferon-tau (IFNT), which, in turn, is responsible for inhibiting luteolysis (corpus luteum regression). When the corpus luteum (ovarian follicle) is active, the production of progesterone (P4) is maintained and the endometrium (mucous membrane that coats the uterine wall) is then prepared for an eventual pregnancy. The study also states that P4 and IFNT regulate Galectin-15 transcription in the endometrial epithelium. Galectin-15 would act in uterine environment, since said Galectin takes part in fixation/adhesion of the trophectoderm of the conceptus to the endometrium of the uterus, thus stimulating biological responses such as adhesion and migration, which are critical events during the elongation phase of the blastocyst, and, consequently, to the evolution of pregnancy.

In a second moment, according to the study by Farmer, J. L. et al, 2008 (*Galectin-15 (LGALS15) Functions in Trophectoderm Migration and Attachment*), Galectin-15 stimulates cell proliferation and inhibition of apoptosis, which are both important events during the implantation phase. The authors proved that, although Galectin-15 gene is present in ovine, caprine and bovine species, the mRNA (messenger RNA) of Galectin-15 is only expressed in the elongation phase of caprines and ovines, the expression of which varies in accordance with the phase of the estrous cycle. Additionally, it is noted that administration of exogenous IFNT by uterine infusion would only increase gene expression of Galectin-15 if the female receives a treatment with P4, thus proving the need of using IFNT and P4 together as inductors of mRNA transcription of Galectin-15.

Satterfield, M. C. et al, 2006 (*Progesterone Regulation of Preimplantation Conceptus Growths and Galectin-15 [LGALS15] in the Ovine Uterus*) concluded that P4 induces gene expression of several proteins secreted by the endometrium, such as Galectin-15 and Secreted Phosphoprotein 1 (SPP1), which are considered to be regulators of the survival and growth of the conceptus, as well as of cellular adherence during the implantation phase. In this sense, the study by Burghardt, R. C. et al, 2009 (*Enhanced Focal Adhesion Assembly Reflects Increased Mechanosensation and Mechanotransduction at Maternal Conceptus Interface and Uterine Wall During Ovine Pregnancy*) mentions that SPP1 and Galectin-15 are mechano-sensors at the uterine environment-conceptus interface.

Following another line of thought, a research conducted by Than, N. G. et al, 2008 (*Emergence of Hormonal and Redox Regulation of Galectin-1 in Placental Mammals: Implication in Maternal-Fetal Immune Tolerance*) concluded that Galectin-1 shows high level of structural conservation, dimerization and linking properties with carbohydrates and integrins (*adhesion proteins*), *suggesting that these properties are conserved among the vertebrates and maintain a standard genic expression among the different placenta types* (*either decidual or not*). The authors also observed that Galectin-1 may impart maternal immunotolerance to fetal alloantigens, regulate the action of Natural Killer (NK) cells of the uterus, and act as T-cell regulating and moderating agents (T-cells are involved in cell immunity). Finally, the authors confirmed the synergistic action of P4 in the stimulation of Galectin-1 production by the endometrium.

Thanks to fertility studies, it is possible to acknowledge that the role of Galectins is associated with the modulation of immune responses, as well as embryo elongation and embryo adhesion to the endometrium.

Galectins are known to be ligands for mammal beta-galactoside lectins and can be expressed by a high number of tissues. These lectins are generally soluble and do not contain a peptide signal, being secreted by a mechanism which is independent from the endoplasmic reticulum and the Golgi complex. As of present day, there are descriptions of 15 mammalian Galectins, all of which having a carbohydrate recognition domain with about 130 amino acid residues.

It is known that the interaction of Galectins with glycans from the surface of immune system cells in extracellular space can modulate the production of cytokine and mediators, cellular adherence, apoptosis, chemotaxis and endocytosis. In the intracellular environment, Galectins can take part in signaling routes and modulate some biological responses, such as apoptosis, regulation of cell growth and pre-mRNA splicing.

Farmer, J. L. et al, 2008 (abovementioned article) also disclose that, apart from Galectin-15 and Galectin-1, other Galectins can be expressed by the endometrium and placenta of mammals, and exhibit important functions in endometrium differentiation, blastocyst implantation and trophoblast differentiation; likewise, Poppovich et al, 2005 (*Galectin-9: a New Endometrial Epithelial Marker for the Mid-and Late-Secretory and Decidual Phases in Human*) disclose the properties of Galectin-9, and Lee et al, 1998 (*Spatio-Temporal Pattern for Expression of Galectin-3 in the Murine Utero-Placental Complex? Evidence for Differential Regulation*) relates to the expression of Galectin-3. Furthermore, there are several other articles in the literature reporting the potential therapeutic use of recombinant Galectins or specific inhibitors of these proteins.

Galectin-1 is a multifunctional molecule which takes part in biological processes such as adhesion, proliferation, differentiation and cell cycles; apoptosis; RNA splicing; control of inflammatory process and adaptative immune response. Endogenous Galectin-1 expression had been already observed in thymic epithelial cells, antigen-primed T cells, activated macrophages, activated B cells (involved in humoral immunity), endothelial cells, stromal cells, and murine lymphoid organs such as the thymus and the lymph node. In view of its immunoregulatory properties, Galectin-1 (either endogenous or exogenous) is an important mediator to prevent fetal loss and/or embryo death.

Galectin-1 can be obtained from mammals (human, bovine, ovine, caprine, equine and/or porcine species) by means of a heterologous expression system in active, sterile, alkylated and endotoxin free form. The method for obtaining recombinant Galectin-1 is widely known in the literature and generally involves the following steps: (i) obtaining a raw extract of bacteria containing Galectin-1; (ii) purifying Galectin-1; (iii) preserving lectin activity of Galectin-1 through alkylation with iodoacetamide; and (iv) removing bacterial endotoxin (LPS) of iodoacetamide-alkylated Galectin-1 preparations. Among the possibilities disclosed in the literature for the tests performed in the present experiment, we have produced Galectin-1 based on the following procedures.

The first step for obtaining recombinant Galectin-1 begins with bacterial culture (preferably *E. coli* rosetta strain) transformed with an expression vector (preferably a pET29a plasmid) containing Galectin-1 gene in 200 mL of LB Broth Base (Invitrogen, Gibco, Carlsbad, Calif., USA) containing 50 µg/mL ampicilin (USB Corporation, USA), which is performed into an orbital shaker at 200 rpm for 16-18 hours at 37° C. After this period, 25 mL of this culture is transferred to 1 L of a previously autoclaved half LB, containing 500 µL ampicilin (50 µg/mL). Further, this bacterial suspension is incubated again for another 2 hours at 37° C. into an orbital shaker at 200 rpm. The optimum bacterial growth rate shows an optical density (OD) range between 0.5-0.5 at 600 nm. Further, 0.36 g of isopropyl-D-thiogalactopyranoside (IPTG, Promega, Wis., USA) diluted into 1 mL of half LB is added to the culture to induce Galectin-1 expression by transformed bacteria. Culture is once again performed into the shaker (37° C.—250 to 300 rpm) for 4 hours. After this period, the bacterial suspension is centrifuged at 5000 g for 15-20 minutes at 4° C. and the culture pellet is once again centrifuged at 3000 g for 15-20 minutes at 4° C. At last, the supernatant is disposed and the pellet is stored at a −80° C. up to the moment of use.

The second step for obtaining recombinant Galectin-1 continues from the bacterial pellet, which undergoes thawing into an ice bath and it is further resuspended in a lysis buffer containing 7 mL of PBS (Phosphate Buffered Saline-NaCl (136.8 mM); KCl (2.7 mM); Na2HPO4 (6.4 mM); KH2PO4 (0.9 mM, pH 7.4); 14 mM mercaptoethanol (2-ME) (Merck-Schuchardt, Germany), 1 tablet of EDTA-free protease inhibitors (Roche Diagnostics GmbH, M, Germany), 1 mL lysozyme-1 mg/mL (Roche Diagnostics GmbH, M, Germany), 10 µL RNAse A Type 3A-10 mg/mL (Sigma-Aldrich) and 10 µL DNAse I Type IV-10 mg/mL (Sigma-Aldrich), and then undergoes incubation for 30 minutes with the lysis buffer in ice bath. Further, the sample is sonicated at 5 cycles of 20 seconds each at 40 W (Sonics Vibra cell; SONICS & MATERIALS INC.); between the cycles, the suspension rests for 15 seconds. The bacterial lysate is then centrifuged at 10,000 g for 45 minutes at 4° C. Then the supernatant is collected and undergoes affinity chromatography on agarose-lactose column (Sigma-Aldrich) with 5 mL bed volume. The nonliBand is eluted with a balance buffer (PBS, added from 2-ME to 14 mM, pH 7.4), and 20 fractions of 2 mL are collected. The affinity-column ligand is eluted with an elution buffer (containing 14 mM lactose, pH 7.4), and 10 fractions of 0.5 mL are collected. The chromatographic procedure is monitored by absorbance reading at 280 nm (UV Mini 1240, Shimadzu) and by polyacrylamide gel electrophoresis. Proteic concentrations in Galectin-1 solutions are determined by spectrometry using absorbance readings at 280 nm or colorimetric assays available in the market and expressed in milligrams of protein by milliliters (mg/mL). The chromatographic fractions obtained through this process for purifying Galectin-1 on agarose-lactose are analyzed by electrophoresis (SDS-PAGE—"Sodium Dodecyl Sulfate Polyacrylamide Gel Electrophoresis"). The samples contained in a reducing and dissociating buffer (final volume 20 µL) are applied to polyacrylamide gel (15%) and undergo eletrophoretic run at constant voltage (150V). Chromatographic fractions of the raw bacterial lysate and the nonligand material were used as samples. For control, a known molecular weight standard is used (LMWH—Low Molecular Weight Calibration kit for Electrophoresis—GE, Amersham—Biosciences, Uppsala, Sweden). Gel is colorized with "Coomassie Brilliant Blue".

Galectin-1 solutions obtained from chromatography on agarose-lactose are kept in an elution buffer with the purpose of preserving lectin activity of this protein, and are stored at −80° C. up to the moment of use. For the assays, these solutions undergo desalination in a PD10 column through molecular exclusion chromatography according to instructions of the manufacturer (Sephadex-G25M; Pharmacia LKB, Uppsala, Sweden). The concentrations of Galectin-1 desalinated solutions are determined by spectrometry or colorimetric reaction, as described above. In order to evaluate the level of preservation of lectin activity (Galectin-1 capability of recognizing sugar) in Galectin-1 purified in agarose-lactose resins, samples of this protein are desalinated in a PD-10 column and immediately rechromatographed in an agarose-lactose column. 20 fractions of 1.0 mL each had been collected. The elution process is monitored by means of proteic concentration (mg/mL). In this last procedure, the elution of Galectin-1 with a wash buffer is considered as an indicator of lectin property loss of this protein, since under such conditions Galectin-1 is not capable of recognizing lactose and therefore it is not retained in the agarose-lactose resin. The oxidation of sulfhydryl groups of Galectin-1 and its denaturation may promote loss of lectin activity of this protein, a property associated with several functions of this molecule. Considering that the purified Galectin-1 solutions were stored at −80° C. and should be thawed prior to use, the impact of said procedures at the hemagglutinant activity of this lectin should be evaluated. Hemagglutination occurs in the presence or absence of a Galectin-1-specific hapten sugar, i.e., lactose (20 mM). Only Galectin-1 preparations exhibiting hemagglutinant activity at concentrations of no more than 2 µM were used at the different assays.

The third step for the preparation of recombinant Galectin-1 involves controlling the lectin activity of alkylated preparations of this lectin through hemagglutination and/or other methods that render possible to determine the preservation of the lectin character of these recombinant Galectin-1 preparations. The oxidation of sulfhydryl groups of Galectin-1 promotes denaturation and loss of lectin activity of this protein. Thus, in order to obtain more stable Galectin-1 samples, preparations of this lectin undergo alkylation with the use of iodoacetamide, a reducing compound which reacts in a covalent manner with sulfhydryl groups, thus generating carboxyamidomethyl-Galectin-1 (alkylated Galectin-1). In brief, 0.037 g iodoacetamide (Protein-Iodoacetamide, Sigma-Aldrich; final concentration of 20 µM) is diluted in 1.0 ml of a purified Galectin-1 solution in the presence of 100 mM lactose. Thereafter, this solution is incubated in an ice bath, protected from light, for 16-18 hours. After incubation, the solution undergoes molecular exclusion chromatography in PD10 to remove free iodoacetamide and lactose. The concentration of alkylated Galectin-1 preparations is determined by spectrometry and expressed on mg/mL, as mentioned above.

The fourth step for the preparation of recombinant Galectin-1 relates to the removal of bacterial endotoxins (LPS). Considering that Galectin-1 had been obtained from gram-negative bacteria, which have LPS (lipopolysaccharide) in the composition of its cell wall, after the step of alkylation with iodoacetamide, Galectin-1 preparations undergo affinity chromatography on a Polymixin B-agarose column (Detoxi-Gel Endotoxin Removing Gel, Pierce, Ill., USA). The effectiveness of the procedure for removing LPS from alkylated Galectin-1 preparations is evaluated by measuring the amount of LPS endotoxin through the use of a QCL-1000 kit (Chromogenic *Limulus Amebocyte* Lysate Assay, Cambrex Company, MD, USA). The active and endotoxin-free, alkylated Galectin-1 preparations then undergo sterilization by filtration (0.22 µm membranes).

As a method for the preparation of recombinant Galectin-1 had been disclosed, it should be noted that any other beta-galactoside-binding lectin or derivatives thereof can be obtained by means of a very similar procedure.

Thus, knowing that Galectin-1 plays an important role in the modulation of immune disorders, inhibiting inflammatory response and modulating T-cell functions in both in vivo and in vitro systems, patent application U.S. Ser. No. 12/175,227 discloses a method for modulating the immune response of said lectin in order to prevent and treat immune disorders, including Hodgkin lymphoma.

With respect to the potential of interaction with other molecules and/or cells, it is known that, in the presence of Galectin-1, dendritic cells become tolerogenic and capable of modulating an immune response in mammals, preventing the development of autoimmune diseases, as well as reversing the rejection of transplants. In this sense, U.S. Ser. No. 12/137,004 patent application discloses a method of preparing a formulation comprising dendritic cells in the presence of said lectin, with the object of treating neoplasms, and autoimmune and infectious diseases.

The study by Blois, S. M. et al, 2007 (*A Pivotal Role for Galectin-1 in Fetomaternal Tolerance*) was based on the results of an experimental treatment model, in which Galectin-1 is intraperitoneally administered in isogenic mice in order to evaluate stress-induced fetal loss caused by noise exposure. It is noted that Galectin-1 expression in mice uterus is highly sensitive to environmental changes, thus compromising the pregnancy of females lead to stress. On the other hand, when mice were treated with recombinant Galectin-1, the occurrence of fetal loss was significantly reduced.

It is known that, to maintain pregnancy, the mother's organism undergoes considerable changes, including hormonal and immune changes. There is evidence that the preparation of the endometrium for embryo implantation is not a mere matter of hormonal stimulation, it depends on the interaction between the blastocyst and the endometrium, and it is also mediated by cytokines, growth factors and adhesion molecules, which are produced and secreted by the endometrium and the blastocyst. Even so, an interaction between different physiological systems could lead to pregnancy losses that cannot be explained by an isolated factor alone.

From the agricultural market point of view, the mechanisms of maternal-fetal immune tolerance in pregnancies deriving from either mating or artificial insemination are still a challenge for reproductive veterinary medicine in view of the immune response against fetal alloantigens.

In this aspect, it should be noted that pregnancy losses generate economical losses, with drastic consequences for breeders, which, in turn, must maintain satisfactory levels of reproductive effectiveness in order to comply with consumers' needs and maintain the profitability of their own property.

Additionally, breeders of both dairy and meat cattle commonly use reproduction techniques to define the sex of the embryo after fertilization. However, in vitro produced embryos that are further transferred to the uterus of receptors do not show satisfactory survival rates due to morphological and structural changes mainly incurring from the maintenance medium, which causes precocious embryo loss.

Furthermore, one of the limitations for the commercial use of reproduction biotechniques is the distance to be covered between the sites of collection and deposition of the male (semen) or female (oocyte) donor's gametes, or of the embryo produced either in vivo or in vitro. It is known that the preservation of cell functions is directly related to pH and temperature variation, among other properties, and thus it is a challenge to maintain it under optimum conditions up to the moment of embryo transfer.

In view of the foregoing, the present invention discloses a solution for the current reproductive difficulties, found mainly in the agricultural market, the main object of which is to promote an increase in the embryo implantation rate in the mother's uterus by supplying to the uterus of the mammal an effective amount of a beta-galactoside-binding lectin or derivatives thereof.

OBJECTS OF THE INVENTION

The object of the present invention is to use an affective amount of a beta-galactoside-binding lectin or derivatives thereof, preferably a member of the group consisting of Galectin-1, Galectin-3, Galectin-9, Galectin-13 or Galectin-15, or derivatives thereof, in order to enhance embryo implantation rate in the mother's uterus on bovine, porcine, ovine, caprine, equine, buffaline, canine, feline and human species, among other species, thus preventing the elimination of the embryo by the mother's immune system.

Another object of the present invention in enhance embryo implantation rate in the uterus of a mammal by transferring a beta-galactoside-binding lectin or derivatives thereof to the reproductive tract of a mammal by means of artificial insemination, in vitro or in vivo embryo transfer, or mating.

Furthermore, it is an object of the present invention to use an effective amount of a beta-galactoside-binding lectin or derivatives thereof in order to promote the fertilization of: (i) fresh, chilled or frozen semen; (ii) fresh, frozen or vitrified oocyte; and (iii) fresh, frozen or vitrified embryo from embryo transfer or in vitro fertilization, or cloned or transgenic embryo.

Another object of the present invention is to provide a beta-galactoside-binding lectin or derivatives thereof to enhance the embryo implantation rate in the uterus of mammals.

At last, it is an object of the present invention to use a product comprising an effective amount of a beta-galactoside-binding lectin or derivatives thereof to enhance the embryo implantation rate in the uterus of mammals.

BRIEF DESCRIPTION OF THE INVENTION

The objects of the present invention are achieved by means of:
(a) a method for increasing the embryo implantation rate in the uterus of mammals by administering to the uterus of a mammal an effective amount of beta-galactoside-binding lectin or derivatives thereof;
(b) use of an effective amount of a beta-galactoside-binding lectin or derivatives thereof for increasing the embryo implantation rate in the uterus of mammals;
(c) a beta-galactoside-binding lectin or derivatives thereof used for increasing the embryo implantation rate in the uterus of mammals; and
(d) a product comprising an effective amount of a beta-galactoside-binding lectin or derivatives thereof for increasing the embryo implantation rate in the uterus of mammals.

DETAILED DESCRIPTION OF THE INVENTION

In the present invention, the implantation rate relates to the number of embryos that actually adhered to the endometrium of mammals after fertilization (union of the male and female gamete), whether or not generated by assisted reproduction technology.

The objects of the present invention are achieved by supplying to the mother's uterus of a mammal, either by uterine or vaginal route, an effective amount of an active form of a beta-galactoside-binding lectin or derivative thereof in a conventional buffered solution, alone or mixed with sperm, oocyte or embryo in a maintenance medium.

The buffered solution aims at maintaining, handling and transferring the semen, oocyte or embryo, and it is preferably a carrier composed of a saline buffered solution (Phosphate Buffered Saline—PSB) or a sterile, stable, endotoxin-free, isotonic physiological serum with a pH between 6.8 and 7.4.

The maintenance medium is a complex and serum-free medium to maintain embryos under atmospheric air for a variable time in accordance with the temperature. A maintenance medium is usually composed of an isotonic buffered solution, which contains essential amino acids, growth factors, enzymes, energy substrates, cell nutrients and antibiotics.

An example of a maintenance medium is a dilution agent, i.e., a diluting liquid added to or mixed with semen to preserve the fertilization ability of the latter. Special dilution agents for freezing also have cryogenic properties, thus enabling transportation, freezing and thawing. Dilution agents consist of isotonic buffer, energetic substrates and cell nutrients, antibiotics, anti-oxidants and cryoprotectants.

The objects of the present invention may also be achieved by supplying, in a simultaneous or subsequent manner, a beta-galactoside-binding lectin or derivative thereof, together with semen, oocyte or embryo to the uterus of a mammal (these steps will be further defined).

Some of the advantages provided by the present invention are as follows: increased reproductive efficiency of livestock; qualitative and quantitative improvements on progeny; reduced length of time between birth and slaughter; reduced feeding costs; increased possibility of heterozygosis; improvements in handling and reduced technical, health and reproductive expenses; among other aspects later described herein.

The present invention comprises the use of a beta-galactoside-binding lectin or derived thereof, preferably Galectin-1, Galectin-3, Galectin-9, Galectin-13 and Galectin-15, for increasing the embryo implantation rate in the uterus of mammals.

The increase of the embryo implantation rate in the uterus of mammals by means of reproductive biotechnologies directly reflects the feasibility of using such procedures as a tool for genetic progress, considering that it improves the results and/or success of techniques to economically viable levels.

Additionally, it is better to use genetic material from genetically superior individuals on reproductive biotechniques, since it maximizes the spread of these animals and provides an alternative to the shortage of clearly superior individuals. Reproductive biotechnologies also allow reduced generation intervals.

In addition, one of today's global challenges is to conquer hunger in a World where cultivatable land areas are shrinking, and with an estimate 50% population growth over the next 25 years. Thus, an increase on embryo implantation rates in the mother's uterus of bovine, porcine, ovine, and other species means increasing food production as a whole, which includes meat production, the demand for which is estimated to double over the next 25 years, reaching more than 127 million tons per year.

The impact of increased embryo implantation rates in the uterus of mammals in productive herds is as follows:
Qualitative and quantitative improvements on progeny—in beef cattle, both in weight and quality—increased daily weight gain, improved quality of marbling, tenderness, flesh flavor, and also improved production of prime cuts, which adds more value to the end product. In dairy herd, it provides increased productivity and improved milk quality.
It also provides a reduced length of time until slaughter, i.e., the increased daily weight gain deriving from genetic improvement reduces the length of time from birth to slaughter by up to 30%. Therefore, the early growth of the animals is significantly increased.
Reduction in feeding costs: in spite of the increasing investments needed to achieve a superior genetic quality, there is a more than satisfactory consideration with the reduction on animal production costs, mainly because of the increase in precocity, which reduces the length of time until slaughter. In view of the above, production costs are reduced in at least 10%.

Increased likelihood of heterozygosis: it becomes more viable to cross-breed cattle breeds that are not adapted to the tropical climate of Brazil, but which provide improvements in carcass, precocity and prolificacy of the herd.

Improvements in handling and reduced technical, health and reproductive expenses: the use of reproductive biotechnologies provides better health conditions, since it prevents the spread of sexually transmitted diseases to cattle, reducing expenses on drugs to treat diseases, and thus reducing production costs.

More particularly, the present invention is a result of tests on the transfer of in vivo produced embryos in female cows in order to prove an increase on embryo implantation rates in the uterus of mammals in the presence of Galectin-1.

EXAMPLES

A single 100 μg dose in-22 μL of a sterile, active, alkylated, and endotoxin-free recombinant human Galectin-1 was administered to the embryo recipients through uterine route. It should be noted that the above dose is dramatically low when compared to the bovine body weight, and favors the biosecurity aspects of the treated females, which, unlike mice (usually used as experimental animals), have the body prepared for a single pregnancy at a time.

In order to assess the effects of Galectin-1 as a regulator agent for fertility in mammals, we have used non-isogenic, confined animals, with normal handling conditions.

Donor bovine females underwent superovulation and were inseminated on D0 (day zero) of fertilization. In parallel, the recipients underwent estrus synchronization protocols in order to ovulate on D0.

On D7 (7th day), the donors entered the phase of collection and evaluation of embryos in morula and/or blastocyst stage. Poor (grade 3), good (grade 2) and excellent (grade 1) embryos were bottled in order to be transferred, on the same day, to the recipients, which were previously selected according to the development of the corpus luteum.

In general, embryo classification is performed in view of morphological parameters, and encompasses three main stages identified according to their stage of development. At the best, the embryo should not have visible fragments, and the cells should have homogeneous size. It should be also noted that not all embryos with excellent morphology are internally healthy, because they are subject to conditions related with the ovule, the spermatozoon and the fertilization process itself.

Embryos on a column of TQC® maintenance medium and Galectin-1 diluted in sterile physiological serum on another column (the embryo does not come into contact with the Galectin solution at the time of bottling) were bottled in the same straw and transferred to the uterus of the recipients, synchronized with the donors, with the aid of an insemination pipette. All of the straw content is transferred at once and, in this embodiment, the embryos and Galectin-1 reach the uterus of the recipient in a separate and simultaneous manner.

The purpose of the tests was to analyze the number of confirmed embryo implantations in the uterus of the mammal on 30 and 60 days after the date of embryo transfer in (i) recipients which received local treatment with Galectin-1 (ii) recipients of a transferred embryo without the presence of Galectin-1. To this end, recipients of a transferred embryo were divided into two distinct groups for each mating (donor×semen), as follows: The Control Group (embryos without the presence of Galectin-1), and the Treated Group (embryos with the presence of Galectin-1).

Pregnancy diagnosis was performed both in the Treated Group and in the Control Group by ultrasound examination at two distinct moments: the first measurement was performed 30 days after embryo transfer (represented in the table below as "P30"), and the second evaluation of the embryo implantation rate in the uterus of a mammal was performed 60 days after embryo transfer (represented in the table below as "P60").

Methodology:

The recipients were bovine females with good milk production and known reproductive ratings. The recipients were Holstein females with high milk production and known reproductive ratings.

The procedure for selection of mating refers to the choice of the breeding animal (semen doses) for each donor. After the collection and evaluation of embryos, about half of the generated embryos were transferred to the uterus of recipients belonging to the CONTROL GROUP and the other half of the embryos was transferred to the uterus of recipients belonging to the TREATED GROUP. There was an effort to equally share the embryos according to the degree of quality shown between the CONTROL GROUP and the TREATED GROUP, in order to render the groups comparable.

Methodology: CONTROL GROUP

The embryo transfer procedure in the Control Group was performed in accordance with the traditional approach to such events, i.e., the embryo transfer occurred in the uterine horn ipsilateral to the corpus luteum (where ovulation occurred at the time of estrus) of the recipients. The straw used, consisting of three main columns, packed one column of TQC® maintenance medium, followed by a column of air, followed by a column of TQC® maintenance medium containing the embryo, followed by another column of air, followed by another column of TQC® maintenance medium. The entire content of the straw was transferred at once.

Methodology: TREATED GROUP

The embryo transfer procedure of the Treated Group was performed in accordance with the traditional approach, i.e., the embryo transfer occurred in the uterine horn ipsilateral to the corpus luteum (where ovulation occurred at the time of estrus) of the recipients. The straw used, consisting of three main columns, packed one column of TQC® maintenance medium, followed by a column of air, followed by a column of TQC® maintenance medium containing the embryo, followed by another column of air, followed by another column of maintenance medium containing Galectin-1. All the straw content was transferred at once and, in this embodiment, the embryos and Galectin-1 reached the uterus of the recipient in a separate and simultaneous manner.

Results:

In the two illustrated tables below, the first column to the left (Repetition) indicates the repetitions of the transfers of embryos generated by each female bovine, corresponding to a total of 12 repetitions. Meanwhile, two other columns are subdivided to separate the results obtained in view of the Control Group and the Treated Group, followed by two other columns showing the relationship between the rates of the additional embryo implantation rate in the uterus of the recipients obtained with the use of Galectin-1 in the procedure.

The column corresponding to the "Quantity Control" indicates the number of embryos generated from embryo transfers without the presence of Galectin-1. The subsequent column to the right (Control P30) is subdivided to show both the number of implantations 30 days after embryo transfer (Quantity 30) with regard to the respective percentage corresponding to the implantation rate during the same period (T30). The same reasoning is used for the subsequent column to the right (Control P60), subdivided in order to demonstrate both the number of implantations 60 days after embryo transfer (Quantity 60) and the respective percentage corresponding to the implantation rate during the same period (T60).

The column corresponding to the "Treated Quantity" indicates the number of embryos generated from embryo transfers in the presence of Galectin-1. The subsequent column to the right (Treated P30) is subdivided to show both the number of implantations 30 days after embryo transfer (Quantity 30) with regard to the respective percentage corresponding to the implantation rate during the same period (T30). The same reasoning is used for the subsequent column to the right (Treated P60), subdivided in order to demonstrate both the number of implantations 60 days after the embryo transfer (Quantity 60) and the respective percentage corresponding to the implantation rate during the same period (T60).

The column corresponding to "Δ implantation rate" is subdivided to indicate the difference in the implantation rate obtained with the Control Group and the Treated Group P30 (Δ30), as well as with the Control Group and the Treated Group P60 (Δ60).

Tables:

TABLE 1

| | | Control P30 | | Control P60 | | | Treated P30 | | Control P60 | | Δ implantation rate | |
|---|---|---|---|---|---|---|---|---|---|---|---|---|
| | Control | Quantity | | Quantity | | Treated | Quantity | | Quantity | | | |
| Repetition | Quantity | 30 | T30 | 60 | T60 | Quantity | 30 | T30 | 60 | T60 | Δ 30 | Δ 60 |
| #01 | 16 | 6 | 37.5% | 4 | 25.0% | 15 | 5 | 33.3% | 5 | 33.3% | −4.2% | 8.3% |
| #02 | 11 | 5 | 45.5% | 4 | 36.4% | 15 | 8 | 53.3% | 8 | 53.3% | 7.9% | 17.0% |
| #03 | 6 | 4 | 66.7% | 4 | 66.7% | 4 | 3 | 75.0% | 2 | 50.0% | 8.3% | −16.7% |
| #04 | 19 | 7 | 36.8% | 6 | 31.6% | 18 | 13 | 72.2% | 9 | 50.0% | 35.4% | 18.4% |
| #05 | 6 | 3 | 50.0% | 3 | 50.0% | 7 | 7 | 100.0% | 7 | 100.0% | 50.0% | 50.0% |
| #06 | 10 | 5 | 50.0% | 5 | 50.0% | 11 | 8 | 72.7% | 4 | 36.4% | 22.7% | −13.6% |
| #07 | 9 | 7 | 77.8% | 5 | 55.6% | 17 | 10 | 58.8% | 9 | 52.9% | 19.0% | −2.6% |
| #08 | 1 | 1 | 100.0% | — | — | 2 | 2 | 100.0% | 2 | 100.0% | — | 100.0% |
| #09 | 8 | 5 | 62.5% | 5 | 62.5% | 6 | 5 | 83.3% | 4 | 66.7% | 20.8% | 4.2% |
| #10 | 6 | 2 | 33.3% | 1 | 16.7% | 10 | 4 | 40.0% | 4 | 40.0% | 6.7% | 23.3% |
| #11 | 5 | — | — | — | — | 5 | 2 | 40.0% | 1 | 20.0% | 40.0% | 20.0% |
| #12 | 6 | — | — | — | — | 6 | 3 | 50.0% | 3 | 50.0% | 50.0% | 50.0% |
| TOTAL | 103 | 45 | 43.7% | 37 | 35.9% | 116 | 70 | 60.3% | 58 | 50.0% | 16.7% | 14.1% |

Results of the implantation rate of grade 1, 2 and 3 embryos from the Control Group (embryo transfer without the presence of Galectin-1) and the Treated Group (embryo transfer in the presence of Galectin-1) after 30 and 60 days, respectively.

As seen in Table 1, the analysis of the total result shows that 30 days after the embryo transfer, the Treated Group showed higher rates of implantation in the mother's uterus, with 60.3% of implantation over 43.7% of the Control Group. The analysis of the final outcome 60 days after embryo transfer showed that the Treated Group rates had 50% implantation in the mother's uterus, while the Control Group had a 35.9%.

In view of the results of Table 1, it is possible to conclude that the use of Galectin-1 increased the number of embryo implantations in the mother's uterus by 16.7 percentage points after 30 days and 14.1 percentage points after 60 days.

TABLE 2

| | | Control P30 | | Control P60 | | | Treated P30 | | Control P60 | | Δ Pregnancy Rate | |
|---|---|---|---|---|---|---|---|---|---|---|---|---|
| | Control | Quantity | | Quantity | | Treated | Quantity | | Quantity | | | |
| Repetition | Quantity | 30 | T30 | 60 | T60 | Quantity | 30 | T30 | 60 | T60 | Δ 30 | Δ 60 |
| #01 | 11 | 4 | 36.4% | 3 | 27.3% | 14 | 5 | 35.7% | 5 | 35.7% | −0.6% | 8.4% |
| #02 | 9 | 4 | 44.4% | 3 | 33.3% | 12 | 6 | 50.0% | 6 | 50.0% | 5.6% | 16.7% |
| #03 | 5 | 3 | 60.0% | 3 | 60.0% | 4 | 3 | 75.0% | 2 | 50.0% | 15.0% | −10.0% |
| #04 | 12 | 4 | 33.3% | 4 | 33.3% | 11 | 8 | 72.7% | 6 | 54.5% | 39.4% | 21.2% |
| #05 | 4 | 2 | 50.0% | 2 | 50.0% | 4 | 4 | 100.0% | 4 | 100.0% | 50.0% | 50.0% |
| #06 | 3 | 1 | 33.3% | 1 | 33.3% | 5 | 3 | 60.0% | 2 | 40.0% | 26.7% | 6.7% |
| #07 | 5 | 3 | 60.0% | 2 | 40.0% | 10 | 6 | 60.0% | 5 | 50.0% | — | 10.0% |
| #08 | 1 | 1 | 100.0% | — | — | 1 | 1 | 100.0% | 1 | 100.0% | — | 100.0% |
| #09 | 3 | 3 | 100.0% | 3 | 100.0% | 1 | 1 | 100.0% | 1 | 100.0% | — | — |
| #10 | 4 | 1 | 25.0% | — | — | 7 | 2 | 28.6% | 2 | 28.6% | 3.6% | 28.6% |

TABLE 2-continued

| | | Control P30 | | Control P60 | | | Treated P30 | | Control P60 | | Δ Pregnancy Rate | |
|---|---|---|---|---|---|---|---|---|---|---|---|---|
| Repetition | Control Quantity | Quantity 30 | T30 | Quantity 60 | T60 | Treated Quantity | Quantity 30 | T30 | Quantity 60 | T60 | Δ 30 | Δ 60 |
| #11 | 4 | — | — | — | — | 3 | 2 | 66.7% | 1 | 33.3% | 66.7% | 33.3% |
| #12 | 2 | — | — | — | — | 2 | 1 | 50.0% | 1 | 50.0% | 50.0% | 50.0% |
| TOTAL | 63 | 26 | 41.3% | 21 | 33.3% | 74 | 42 | 56.8% | 36 | 48.6% | 15.5% | 15.3% |

Results of the implantation rate considering only grade 2 embryos from the Control Group (embryo transfer without the presence of Galectin-1) and the Treated Group (embryo transfer in the presence of Galectin-1) after 30 and 60 days, respectively.

The results listed in Table 2 showed that the Treated Group had a higher number of implantations in the mother's uterus with a 56.8% implantation rate over 41.3% of implantation achieved by the Control Group 30 days after embryo transfer of grade 2 embryos. The analysis of the final outcome 60 days after the transfer of grade 2 embryos showed that the Treated Group rates had a 48.6% implantation in the mother's uterus, while the Control Group had a 33.9% rate.

In view of the results shown in Table 2, it is possible to conclude that Galectin-1 supplied to the uterus of a bovine recipient of the Treated Group increased the number of implantations by 15.5 percentage points after 30 days and by 15.3 percentage points after 60 days, enhancing the implantation rates of grade 2 embryos in the uterus of cows.

Considering that, in this experiment, recombinant human Galectin-1 acts as an antigen in the mother's uterus of bovines, mainly because it comes from different species, studies are being made in order to prove (i) a greater interaction between Galectins and glycans from the same species, and, consequently, (ii) a better performance of Galectin-1 in the increase of the embryo implantation rate in the mother's uterus of mammals.

The physiological mechanisms triggered by Galectin-1 that make it possible to increase the embryo implantation rate in the uterus of mammals are still being studied, since the pregnancies of the bovine recipients to which embryos had been transferred did not come into term yet.

In bovines, the placenta has numerous units with different sizes and shapes which, in turn, consist in a swell of interdigitated fetal villosities with cryptform invaginations reunited in the uterus. For the maintenance of pregnancy, the embryo must participate by sending signs of its existence in the uterine environment through the production of IFNT. Thus, luteolysis remains inhibited and, consequently, P4 levels are kept high. Therefore, both IFNT and P4 stimulate the mRNA to increase the level of Galectins in the uterus. After the maternal environment recognizes and accepts the embryo, the trophoblast cells differentiate and unite to the cells of the uterine epithelium, thus coming into direct contact with maternal tissues.

It is believed, therefore, that the increased embryo implantation rate in the mother's uterus of mammals is explained by the participation of Galectin-1 in the regulation of the mechanisms related to immune tolerance and/or in promoting the process of blastocyst elongation and embryo adhesion in the endometrium.

The present invention further discloses that a beta-galactoside-binding lectin or derived thereof, preferably selected from Galectin-1, Galectin-3, Galectin-9, Galectin-13 or Galectin-15, or a derivative thereof, can be used to act as agent to regulate the fertility of semen, oocytes or embryos, thereby increasing the embryo implantation rate in the uterus of mammals.

The amount of beta-galactoside-binding lectin or a derivative thereof supplied to the mother's uterus of a mammal may vary in accordance with the body weight of the species, and its concentration rate should preferably range from 0.0000001 to 1.0 mg per kilogram of body weight of the mammal.

In one embodiment, the beta-galactoside-binding lectin or derived thereof is diluted in a buffered solution, preferably phosphate buffered saline (PBS) or physiological serum, and it is supplied to the uterus by means of a conventional straw mixed with semen, oocyte or embryo kept in a maintenance medium (capable of maintaining the survival of cells and the biological integrity during handling, transporting, freezing and thawing), so that the entire content of the straw is supplied to the uterus of the mammal at once.

In a preferred variation, the beta-galactoside-binding lectin or derived thereof is packed in two steps, in a separate manner and subsequent to semen, oocyte or embryo, and, in this procedure, two filling straws are used. In the first application, the semen, oocyte or embryo is put into a maintenance medium and packed in a conventional straw, so that all content is supplied to the uterus of the mammal. In the second application, the beta-galactoside-binding lectin or derivative thereof diluted in a buffered solution is packed in a different straw and, subsequently, it is supplied to the uterus of the mammal. The lapse of time between the supply of beta-galactoside-binding lectin or a derivative thereof and the supply of sperm, oocyte or embryo will depend, essentially, on the mammalian species handled and the method of treatment employed and may extend up to 17 days in accordance with the treatment being employed.

It is also disclosed that the beta-galactoside-binding lectin or a derivative thereof diluted in a buffered solution is packed on a column of a given conventional straw, interspersed between other columns containing sperm, oocyte or embryo in a maintenance medium, so that all the straw content is subsequently supplied to the uterus of the mammal.

In all variations provided, the beta-galactoside-binding lectin or derivative thereof, together with semen, oocyte or embryo, is administered through uterine or vaginal route. The semen can be in fresh, chilled or frozen; the oocyte can be fresh, frozen or vitrified; and the embryo can be fresh, frozen or vitrified, and may also be from embryo transfer, in vitro fertilization, as well as a clone or a transgenic embryo.

Moreover, it is known that in vitro embryo production systems allow the determination of the sex of the embryo after fertilization, and thus said systems are an important tool dairy cattle and beef cattle breeders. Nevertheless, in vitro produced embryos do not exhibit satisfactory survival rates in the uterus of mammals. Hence, the present invention provides a solution to regulate semen, oocyte or embryo fertility, thus increasing the embryo implantation rate in the uterus of mammals.

On the other hand, one of the limitations for the commercial application of reproduction biotechnologies is the distance to be traveled between the location for collection of semen, oocyte or donor's embryo and the location where the recipient species is; as well as the distance separating the donor species from the recipient species. In this sense, cryopreservation (freezing process) and vitrification (ultra-fast freezing method) have become a common practice in animal production. However, although cryopreservation and vitrification techniques have commercial advantages, the spermatozoons may suffer changes in the membrane, early capability, DNA changes and oxidative stress during freezing, which compromises their fertility.

In a preferred embodiment, the present invention discloses the use of a product comprising an effective amount of a beta-galactoside-binding lectin or derivatives thereof to enhance the embryo implantation rate in the uterus of mammals.

As several examples of preferred embodiments had been disclosed, it should be understood that the scope of the present invention encompasses other possible embodiments and it is only limited by the content of the appended claims, including therein the possible equivalents.

The invention claimed is:

1. A method for increasing embryo implantation rate in the uterus of mammals, characterized in that it comprises administering to the uterus of a mammal an effective amount of a galectin or an alkylated form thereof that binds beta-galactoside simultaneously with or up to 17 days after administration of semen, an oocyte, or an embryo.

2. A method according to claim 1, characterized in that an amount ranging from 0.0001 to 1.0 mg of an active form of a galectin or an alkylated form thereof is administered per kilogram of body weight of the mammal.

3. A method according to claim 2, characterized in that the active form of a galectin or an alkylated form thereof is in the form of a sterile, stable, endotoxin-free, isotonic carrier having a pH between 6.8 and 7.4.

4. A method according to claim 3, characterized in that the carrier is a buffered solution.

5. A method according to claim 4, characterized in that the buffered solution is selected from a saline phosphate buffered solution (PBS) or physiological serum.

6. A method according to claim 1, characterized in that the galectin or alkylated form thereof is selected from Galectin-1, Galectin-3, Galectin-9, Galectin-13, Galectin-15 or an alkylated thereof.

7. A method according to claim 1, characterized in that the galectin or alkylated form thereof is supplied to the uterus of the mammal mixed with semen, oocyte or embryo.

8. A method according to claim 7, characterized in that the semen, oocyte or embryo is provided in a maintenance medium.

9. A method according to claim 8, characterized in that the semen is fresh, chilled or frozen.

10. A method according to a claim 8, characterized in that the embryo is fresh, frozen or vitrified, and comes from embryo transfer (ET), in vitro fertilization (IVF), a clone or a transgenic embryo.

11. A method according to a claim 8, characterized in that the oocyte is fresh, chilled or vitrified.

12. A method according claim 7, characterized in that the galectin or alkylated form thereof, together with semen, oocyte or embryo, is administered through uterine or vaginal route.

13. A method according to claim 1, characterized in that the galectin or alkylated form thereof is supplied to the uterus of the mammal separately from but simultaneously with the administration of semen, oocyte or embryo.

14. A method according to claim 1, characterized in that the galectin or alkylated form thereof is supplied to the uterus of the mammal separately from and subsequently to the administration of semen, oocyte or embryo.

15. A method according to claim 14, characterized in that the galectin or alkylated form thereof is supplied to the uterus of the mammal together with and semen, oocyte or embryo in a subsequent manner, and the lapse of time between the supply of galectin or alkylated form thereof, and the supply of semen, oocyte or embryo extends up to 17 days.

* * * * *